(12) United States Patent
Kanome et al.

(10) Patent No.: US 8,148,153 B2
(45) Date of Patent: Apr. 3, 2012

(54) SUBSTRATE FOR CELL CULTURE, PRODUCING METHOD THEREOF AND SCREENING METHOD FOR CELL CULTURE CONDITIONS UTILIZING THE SAME

(75) Inventors: Osamu Kanome, Yokohama (JP); Kohei Watanabe, Chofu (JP); Takeshi Miyazaki, Yokohama (JP); Tomoyo Fujiyama, Nishitokyo (JP); Ryoichi Matsuda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 14 days.

(21) Appl. No.: 12/711,212

(22) Filed: Feb. 23, 2010

(65) Prior Publication Data

US 2010/0151510 A1 Jun. 17, 2010

Related U.S. Application Data

(62) Division of application No. 10/582,099, filed as application No. PCT/JP2004/018962 on Dec. 13, 2004.

(30) Foreign Application Priority Data

Dec. 16, 2003 (JP) ................................. 2003-418560

(51) Int. Cl.
*C12N 5/00* (2006.01)
(52) U.S. Cl. ....................................................... 435/405
(58) Field of Classification Search .................. None
See application file for complete search history.

(56) References Cited

U.S. PATENT DOCUMENTS

| | | | |
|---|---|---|---|
| 4,990,075 A * | 2/1991 | Wogoman ..................... 422/417 |
| 5,108,926 A | 4/1992 | Klebe |
| 5,147,607 A * | 9/1992 | Mochida ....................... 422/417 |
| 5,370,842 A | 12/1994 | Miyazaki et al. |
| 5,380,490 A | 1/1995 | Hoshi et al. |
| 5,512,446 A | 4/1996 | Miyazaki et al. |
| 5,534,441 A | 7/1996 | Miyazaki et al. |
| 5,601,983 A | 2/1997 | Takayama et al. |
| 5,624,798 A | 4/1997 | Yamamoto et al. |
| 5,670,315 A | 9/1997 | Yamamoto et al. |
| 5,679,516 A | 10/1997 | Okamoto et al. |
| 5,679,581 A | 10/1997 | Miyazaki et al. |
| 5,700,647 A | 12/1997 | Miyazaki et al. |
| 5,750,346 A | 5/1998 | Bridgham et al. |
| 5,846,730 A | 12/1998 | Miyazaki et al. |
| 6,022,961 A | 2/2000 | Yamamoto et al. |
| 6,171,856 B1 | 1/2001 | Thigpen et al. |
| 6,322,971 B1 | 11/2001 | Chetverin et al. |
| 6,818,435 B2 * | 11/2004 | Carvalho et al. ............ 435/286.5 |
| 6,833,112 B2 | 12/2004 | Hoummady |
| 7,419,820 B2 | 9/2008 | Watanabe et al. |
| 7,497,997 B2 * | 3/2009 | Glezer et al. .................. 422/104 |
| 7,541,195 B2 * | 6/2009 | Tashiro et al. ................ 436/518 |
| 7,632,462 B2 | 12/2009 | Holtlund et al. |
| 7,981,664 B1 * | 7/2011 | Dultz ........................ 435/287.2 |
| 2002/0055111 A1 * | 5/2002 | Chen et al. ....................... 435/6 |
| 2002/0177221 A1 | 11/2002 | Nishiguchi et al. |
| 2002/0182721 A1 | 12/2002 | Nishiguchi et al. |
| 2004/0096866 A1 * | 5/2004 | Hofmann et al. ................. 435/6 |
| 2006/0177877 A1 | 8/2006 | Stockwell et al. |
| 2007/0248571 A1 | 10/2007 | Masada et al. |

FOREIGN PATENT DOCUMENTS

| | | |
|---|---|---|
| JP | 2000-512009 | 9/2000 |
| JP | 2002-328124 | 11/2002 |
| JP | 2002-355025 | 12/2002 |
| JP | 2002-355026 | 12/2002 |
| JP | 2003-33177 | 2/2003 |
| JP | 2003-322630 | 11/2003 |
| JP | 2003-322633 | 11/2003 |
| WO | 97/45730 | 12/1997 |
| WO | 01/96019 | 12/2001 |

OTHER PUBLICATIONS

Yoshihiro Ito, "Biomaterial to Communicate with Cells: Adhesion and Gene Expression of Cells", Protein, Nucleic Acid and Enzyme, vol. 45, No. 5, 2000, pp. 727-734. (with translation).

* cited by examiner

*Primary Examiner* — Ann Lam
(74) *Attorney, Agent, or Firm* — Fitzpatrick, Cella, Harper & Scinto

(57) ABSTRACT

A cell culture substrate having at least one area for culturing a cell on a substrate, characterized in that the culturing area comprises an area releasably holding a biologically active substance having a biological activity to the cell and an area for immobilizing a biologically active substance having a biological activity to the cell.

8 Claims, 2 Drawing Sheets

SUBSTRATE FOR CELL CULTURE, PRODUCING METHOD THEREOF AND SCREENING METHOD FOR CELL CULTURE CONDITIONS UTILIZING THE SAME

This application is a divisional of Application No. 10/582,099, which was the National Stage of International Application No. PCT/JP2004/018962, filed Dec. 13, 2004. The contents of each of the foregoing applications is incorporated herein by reference.

TECHNICAL FIELD

The present invention relates to a substrate for culturing cells for identifying a biologically active substance having a biological activity to cells, a producing method thereof and a screening method for cell culture conditions utilizing the same.

BACKGROUND ART

In recent years, studies of culturing animal or plant cells under various conditions and studies of products of certain cell cultures have been actively carried out. Particularly, studies on production of substances, of which artificial synthesis is impossible or very difficult, utilizing certain cell activities are carried out in various fields. Also studies are carried out to identify substances that affect cellular growth and differentiation so as to obtain proliferation or differentiation of certain cells according to the purpose. Also with the rapid progress in cell engineering and medical engineering, minute biosensors, artificial organs, neurocomputers and the like are attracting attentions and actively studied. In order to utilize cells in vitro as explained above, it is essential to dispose cells to control their proliferation, differentiation and substance production in a desired manner. However, the mechanisms of cell disposition, cell proliferation and differentiation and substance production have not been sufficiently clarified, so that the cell culture under controlled conditions is extremely difficult impeding researches utilizing cells.

Also tailor-made therapy considering personal difference in the drug sensitivity, of which concept has recently been widely recognized, is strongly desired, but the influence of biologically active substances has been investigated only on the function of respective substances, mainly because of technical reasons, and there has not been established an effective method for easily investigating effects of plural drugs at the same time, or required doses thereof or combined effects thereof.

For controlling cell disposition, U.S. Pat. No. 5,108,926 describes formation a pattern on a substrate by applying a cell-adhering protein using an ink jet printer and cell culture thereon. This method allows to culture cells on the formed pattern of the cell-adhering protein, but not to control the proliferation, differentiation and substance production of the cells or to achieve screening of culture conditions for cellular differentiation, proliferation or survival using cells. Also "Protein, Nucleic acid and Enzyme", vol. 45, 727-734 (2000) describes fixation of a cell growth factor that influences the cell proliferation and differentiation on a substrate using photolithography, thereby investigating its influence on the cell proliferation and differentiation. However, the substrate on which the cell growth factor is immobilized is not used for screening of culture conditions for cellular differentiation, proliferation or survival using cells, and the photolithography has problems that a rare biological substance is wasted and the production process is complicated requiring repetition of exposure and development steps.

Japanese translation of PCT international application No. 2000-512009 proposes a method for screening of culture conditions for cellular differentiation, proliferation or survival using cells by immobilizing onto a substrate a substance that affects cell adhesion. In this method, reactive functional groups provided on the substrate and the cell-adhering substance are bonded through a divalent crosslinking reagent. Photolithographic technology is utilized in bonding the reactive functional group and the cell-adhering substance, which has problems, in addition to the aforementioned problems, that when plural cell-adhering substances are immobilized, it is extremely difficult to avoid a situation where an already immobilized substance and a substance to be newly immobilized are bonded by the divalent crosslinking reagent in undesired positions, that is, it is extremely difficult to arrange cell-adhering substances in desired positions. Also the proposed method is not to fix a substance influencing the cell proliferation, differentiation and substance production. That method is to screen cells by immobilizing cells in individual wells through the immobilized adhering substance, culturing the cells in a culture medium and detecting a certain substance produced by the cells. Thus it is not intended for screening a substance which influences at least one of adhesive property, proliferation, differentiation, survival, maintenance of an undifferentiated state, death and material production of cells, as intended in the present invention.

Also Japanese Patent Application Laid-open No. 2002-355025 discloses a method of forming a screening substrate characterized in immobilizing plural screening substances by using liquid discharge means in desired areas of a base, thereby providing different screening functions. In this invention, since the substances for screening are immobilized to the screening substrate, cells often cannot intake the screening substance into the cells. Therefore, this invention is not effective, for screening substances and conditions that affect at least one of proliferation, differentiation, survival, maintenance of an undifferentiated state, death and substance production when the screening substance is taken into the cells.

Also Japanese Patent Application Laid-open No. 2002-328124 discloses a screening method with a higher order combination of biological active substances, but this is to evaluate an effect of a function of biological active substances provided but not immobilized to a substrate, so it cannot be used for screening effects of biological active substances that affect the living body in a state immobilized on a substrate without entering the cells, or an effect induced by successive additions of biological active substances.

Also Japanese Patent Application Laid-open No. 2003-33177 proposes a simple assay of chemical substances such as drugs or toxic substances, preparing a cell array divided into plural areas and providing a biologically active substance to each area to carry out simultaneous screening of plural samples. In such a method, however, each biologically active substance is provided to the cultured cells by using a dispensing means. Thus there is a danger of contamination in the dispensing step and it requires a specific apparatus for dispensing the biologically active substances, far from convenient use.

DISCLOSURE OF THE INVENTION

In consideration of the foregoing, the present invention aims to provide a cell culture kit which can solve the technical problems in the aforementioned prior techniques and enables simultaneous evaluation of the effects of plural biologically active substances in a immobilized or dissolved state through simple steps, as well as a producing method of such a kit and a screening method utilizing the same, thereby providing a basic technology for further advance in cell engineering and for various cell-utilizing devices. Another object of the present invention is to provide a screening method utilizing such a cell culture kit, for screening a substance and/or condition which influences at least one of all the biological activities of a cell. Still another object of the invention is to provide a method of screening a biologically active substance and/or condition utilizing cells.

The present invention includes following aspects:

(1) A cell culture substrate having at least one area for culturing a cell on a substrate, characterized in that the culturing area comprises an area for holding a biologically active substance having a biological activity to the cell and an area for immobilizing a biologically active substance having a biological activity to the cell.

(2) The cell culture substrate according to the above (1), wherein a plurality of biologically active substances are held or immobilized in at least either of the holding area and the immobilizing area in each culture area.

(3) The cell culture substrate according to the above (1), wherein the biologically active substance in the holding area is held in such a manner that it is released in a culture liquid when coming in contact with the culture liquid.

(4) The cell culture substrate according to the above (1), wherein at least either of the holding area and the immobilizing area in the culture area is provided in plural units.

(5) The cell culture substrate according to the above (1), wherein the holding area and the immobilizing area include areas between which the kind of the biologically active substance or the combination of plural biologically active substances is different, and one or more combinations are included.

(6) The cell culture substrate according to the above (1), wherein the holding areas and the immobilizing areas include at least a combination of the areas different in a density of the biologically active substance.

(7) The cell culture substrate according to the above (1), wherein the culture area is formed in a recess formed on a surface of the substrate.

(8) The cell culture substrate according to the above (1), wherein the culture area is surrounded by a wall-shaped structure.

(9) The cell culture substrate according to the above (1), wherein at least either of the holding area and the immobilizing area includes an area in which a biologically active substance is held or immobilized across a supporting layer provided on a surface of the substrate.

(10) The cell culture substrate according to the above (1), wherein the holding area is provided at a predetermined height from a lower end of the culture area.

(11) The cell culture substrate according to the above (10), wherein a culture area includes two or more holding areas provided in positions different in distances from a lower end of the culture area.

(12) The cell culture substrate according to the above (1), characterized in that the biologically active substance can be control-released or a biologically active substance having a control-release property can be liberated from the holding area.

(13) The cell culture substrate according to the above (1), wherein the culture area is provided in a recess, of which at least one of walls is inclined from a bottom portion to an upper portion, and an aperture of the recess has an area wider than a bottom area of the recess.

(14) A method for producing a cell culture substrate according to any one the above (1)-(13), characterized in that liquid discharge means is utilized for providing a biologically active substance to at least one of the holding area and the immobilizing area.

(15) The method according to the above (14), wherein the liquid discharge means is discharge means by a thermal ink jet method.

(16) The method according to the above (14), wherein the liquid discharge means is discharge means by a piezo ink jet method.

(17) The method according to the above (14), further comprising a step of carrying out fixation of the biologically active substance by applying an immobilizing energy from the exterior.

(18) A method for screening a cell culture condition utilizing a cell culture substrate according to any of claims 1-13, the method comprising the steps of:
filling the culture area with a culture liquid and culturing cells in a state where a biologically active substance immobilized in an immobilizing area of the culture area is in contact with the culture liquid; and
contacting the culture liquid with the holding area thereby liberating a biologically active substance present in the holding area into the culture liquid.

(19) The method according to the above (18), further comprising the step of replenishing the culture liquid with a substance necessary for screening a cell culture condition.

(20) The method according to the above (18), further comprising the step of observing a shape change of cells.

(21) The method according to the above (20), wherein cells are stained for evaluation.

(22) The method according to the above (18), further comprising the step of carrying out a quantitative determination of a substance synthesized in the cells.

(23) The method according to the above (18), further comprising the step of carrying out a quantitative determination of a substance incorporated in the cells.

(24) The method according to the above (22) or (23), further comprising a step of carrying out a quantitative determination of the substance by at least one of a radiation dose measurement, a fluorescence amount measurement, a light emission amount measurement and an optical absorbance measurement.

The screening method of the invention enables identification of a factor required for cell proliferation, differentiation, survival, maintenance of undifferentiated state, death or production, which allows determination of an effective cell-culturing method. Also according to the present invention, substances can be screened not only in their solid phase but also in their liquid phase, that is, screening is carried out under conditions closer to in vivo conditions using combinations of biologically active substances in their immobilized state or dissolved state. The present invention also allows investigation of difference in the effect of a substance in its solid phase and in its liquid phase, and evaluation of individual sensitivity to a drug or an endocrine perturbing substance, so-called environmental hormone. It is also possible, based on the result of such evaluation, to determine a tailor made therapeutic method for individuals. It is furthermore possible to screen useful substances having biological activities to cells using cells.

The cell culture substrate of the invention can be produced employing an ink jet method as the liquid discharge means, enabling simultaneous action of plural substances on the cells at various concentrations by choosing liquid species and controlling a number of liquid droplets. Also the culture substrate of the invention allows precise re-solubilization of plural substances in a cell culture liquid, enabling exact evaluation of an effect of a system comprised of plural biologically active substances to the cell proliferation, differentiation and survival, which has been difficult to evaluate in the prior technology. Also a successive addition of biologically active substances or change in combination is easy. Therefore, the effect of such conditions can be studied easily and effectively. Furthermore, the cell culture substrate of the invention can be easily produced in a large scale, and stored stably and used whenever desired as a screening substrate.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the description, illustrate embodiments of the invention and, together with the description, serve to explain the principles of the invention.

BEST MODE FOR CARRYING OUT THE INVENTION

Figure 1:
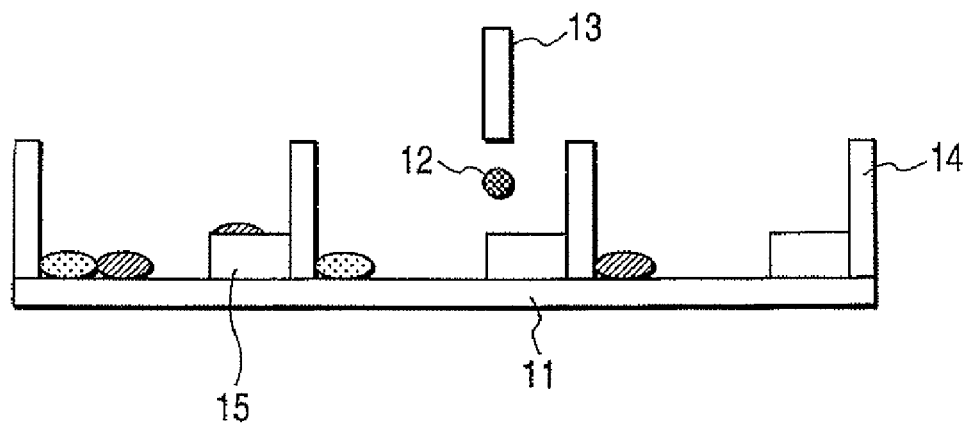
FIG. 1 illustrates an example of preparation of a cell culture substrate of the present invention.

Preferred embodiments of the present invention will now be described in detail in accordance with the accompanying drawings.

A best mode of the present invention is a cell culture substrate 1 having a biologically active substance, formed by immobilizing and temporarily immobilizing (holding) on a substrate 1 a biologically active substance that affects at least one function selected from proliferation, differentiation, survival, maintenance of an undifferentiated state and death. Preferably, the biologically active substance can control the location of the cell adhesion to the substrate 1, as well as a cellular function selected from proliferation (including promotion and suppression), differentiation (including promotion and suppression), survival, maintenance of an undifferentiated state, and cell death (apoptosis). Examples of such substance include an extracellular matrix protein, an antibody having a specific binding ability to the cell surface, a cytokine, and a chemical substance that affects cell proliferation or differentiation when taken into the cells. Examples of the extracellular matrix protein include collagen, fibronectin and laminin. Cytokine includes a cell growth factor and a hormone, and the cell growth factor includes a nerve growth factor (NGF), an epithelium growth factor (EGF), a basic fibroblast growth factor (bFGF), an osteogenesis factor (BMP-2), an insulin-like growth factor (IGF-I), and a tumor necrosis factor (TNF). Examples of hormone include insulin and adrenalin. In one holding area, one or more biologically active substances may be immobilized or held to the substrate 1. For example, by immobilizing and holding two or more biologically active substances of different functions within the same immobilizing and holding areas, there can be achieved a further advanced control of at least one of proliferation, differentiation, survival, maintenance of an undifferentiated state, and death. The biologically active substance absorbed by a binder such as PVA (polyvinyl alcohol) in a liquid state can be temporarily immobilized (held) at a desired position of the substrate 1. Alternatively, a solution of a biologically active substance in an amount as small as several microliters or less can be applied and dried to hold it at a desired position, e.g., on a base 11 and/or a wall 14 and/or a stage 15. Also the held biologically active substance on the substrate 1 may be different in separate holding areas depending on the purpose of cell culture. Also when plural biologically active substances are fixed in predetermined positions in a single area of the substrate 1, the combination of the plural biologically active substances may be the same or different between the separate fixation areas. Also, even when the combination of the biologically active substances is the same between the separate fixation areas, it is useful to vary concentration ratios. Use of such a substrate 1 allows cell culture with control of at least one function selected from cell adhesion, proliferation, differentiation, maintenance of undifferentiated state, death etc. under various conditions. In consideration of a possibility that plural biologically active substances affect the cell culture cooperatively, information of the environment having a largest influence on the cell culture can be obtained by varying the combination of the biologically active substances or concentration ratio thereof in the holding areas. To immobilize a biologically active substance onto the base 11, the active substance may be subjected to a treatment necessary for immobilization in advance or the base may be subjected to a necessary treatment. Treatment of the active substance includes introduction of a functional group required for covalent bonding such as amino, carboxyl, disulfide, epoxy, carbodiimide, and maleimide, or binding of a chargeable compound necessary for binding through electrostatic attraction such as fine particles of a metal or inorganic oxide, cationic or anionic polymers. A substance that allows binding through biological affinity such as avidin and biotin, and antigen and antibody can be also used. Alternatively, the surface of the base may be coated with a polymer or a silane coupling agent to introduce a functional group necessary for covalent bonding such as amino, carboxyl, disulfide, epoxy, carbodiimide, and maleimide. Alternatively, an electroconductive layer or semiconductive layer mage be formed on the substrate in advance to charge the base surface. The layer may be formed with a metal such as gold, silver, platinum and iron, an inorganic oxide such as indium-tin oxide, titanium oxide and zinc oxide, or an electroconductive polymer such as polyacetylene, polypyrrole, polyaniline and polythiophene. Further, the base is provided with a substance having an affinity with the substance introduced to the biologically active substance, such as biotin, avidin, antibody or antigen, protein A that binds to antibodies. Introduction of such a material makes the binding force between the base 11 surface and the biologically active substance strong.

Energy can be supplied from outside by heating or irradiation for accelerating binding between the base 11 and the biologically active substance.

One or more stages 15 may be provided in the cell culture substrate 1 of the invention varying the height from the base 11. Plural stage 15 at different distances from the base 11 is effective to study the influence of timing of supply of the biologically active substance, because the volume of the culture liquid can be increased once or more during culture to dissolve the held biologically active substance at a timing different from well to well. By providing holding areas on the base 11, on the stage 15 and/or on the wall 14 with varying heights from the base 11, and by gradually increasing the amount of the culture medium during cell culture, it is possible to control feeding of plural biologically active substances with time.

A cell employable in the present invention may be any procaryotic or eucaryotic cells. For example, there can be employed a bacteria cell, an yeast cell, a protozoa cell, a neuron, a fibroblast, a smooth muscle cell, a skeletal muscle cell, a gliocyte, an embryonic stem cell, a hematopoletic stem cell, a mast cell, a fat cell, a nerve stem cell or an immune cell including T cell and B cell, or a cluster thereof including transformed or non-transformed cells.

The base 11 and/or wall 14 and/or stage 15 of the substrate of the invention can be made of any material of any shape, as long as the biologically active substance can be held in a stable manner. More specifically, a glass plate, a plastic plate, a plastic sheet, a polymer film or paper can be employed advantageously. Also the substrate 1 may be transparent, opaque, or colored. Also in order to hold a biologically active substance on the base 11 and/or wall 14 and/or stage 15 or to improve stability of the biologically active substance on the base 11 and/or wall 14 and/or stage 15, the base 11 and/or wall 14 and/or stage 15 or a part thereof may be subjected to a treatment with a chemical substance or a radiation. In case the stage 15 is absent, the wall 14 is preferably inclined in order to provide a holding area. The angle of inclination is preferably about 25 to 65°, since an angle close to vertical makes adjustment of the height of the holding area difficult and a shallower angle reduces the density of wells in the preparation of the cell culture substrate. For forming wells, upright or inclined wall structures in the cell culture substrate, there can be employed, for example, an injection molding, a liquid molding, an adhesion of a chip by thermal fusion or with an adhesive, or a press molding in a metal mold.

Also the base 11 and/or wall 14 and/or stage 15 may be formed in a concave portion (recess or well) formed on the substrate surface. Such configuration can facilitate positioning of a liquid droplet, provided by liquid discharge means onto a predetermined position on the substrate, and allows a cell culture using a different culture liquid well to well. Further in a well, an area holding a biologically active substance or a group of areas each holding a biologically active substance may be provided, whereby cell culture can be carried out for the respective areas or groups using different culture liquids.

A method for producing the cell culture substrate 1 of the above-described configuration will be explained with reference to FIG. 1. First, a base 11 may be subjected to a pretreatment as described above, if necessary. More specifically, the base 11 is washed to eliminate undesired substances and may be subjected to various chemical or physical treatments such as radiation including UV irradiation, and corona discharge. Also it is possible, if necessary, to apply a polymer material or a silane coupling agent on the base 11 and/or wall 14 and/or stage 15 or a part thereof.

A biologically active substance is positioned on such base 11 and/or wall 14 and/or stage 15. Liquid discharge means 13, for example, is employed for positioning. The liquid discharge means is capable of discharging a liquid droplet of a volume of 100 nl or less per drop, more specifically about 1 pl to 1 nl, such as a micropipette, a microdispenser, or a discharge apparatus of ink jet method. A discharge apparatus of ink jet method can be employed particularly advantageously because it is inexpensive and can discharge a minute liquid droplet at a controlled position. Furthermore, among the ink jet methods, a thermal ink jet method and a piezo ink jet method can be employed advantageously. A discharge apparatus of the thermal ink jet method, being easy in preparation of fine discharge ports, can discharge a liquid containing a biologically active substance at predetermined positions at a high density, whereby the biologically active substance can be positioned highly precisely on the base 11. Also a discharge apparatus of the piezo ink jet method, in which a discharge energy is generated by displacement of a piezoelectric element, can discharge a liquid 12 containing a biologically active substance without giving a thermal stress thereto.

The biologically active substance is dissolved or dispersed in an appropriate solvent for discharge. Any solvent (dispersion medium) may be employed as long as it can stably dissolve or disperse the biologically active substance, but water is employed advantageously. Water is present in 30 mass % or higher, preferably 50 mass % or higher. Preferably, water is ion-exchanged water (deionized water) or various buffers for stably dissolving the biologically active substance. Also, if necessary, a water-soluble solvent may be employed. The amount of each water-soluble solvent to be added is 50 mass % or less, preferably 30 mass % or less. Any water-soluble solvent may be employed as long as it is soluble in water, and examples include an alkyl alcohol with 1 to 4 carbon atoms such as methyl alcohol, ethyl alcohol, n-propyl alcohol, isopropyl alcohol, n-butyl alcohol, sec-butyl alcohol, or t-butyl alcohol; an amide such as dimethylformamide or dimethylacetamide; a ketone or a ketoalcohol such as acetone or diacetone alcohol; an ether such as tetrahydrofuran or dioxane; an polyalkylene glycol such as polyethylene glycol, or polypropylene glycol; an alkylene glycol in which an alkylene group has 2-6 carbon atoms such as ethylene glycol, propylene glycol, butylenes glycol, triethylene glycol, 1,2,6-hexanetriol, thiodiglycol, hexylene glycol or diethylene glycol; glycerin; a lower alkyl ether of a polyhydric alcohol such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, or triethylene glycol monobutyl ether; N-methyl-2-pyrrolidone, 2-pyrrolidone and 1,3-dimethyl-2-imidazoline. These solvents may be suitably selected in one or more kinds. Among these water-soluble organic solvents, there is preferred a polyhydric alcohol such as diethylene glycol, or a lower alkyl ether such as triethylene glycol monomethyl ether. In case of thermal ink jet method, addition of an alcohol such as ethanol or isopropyl alcohol or a lower alkyl ether of a polyhydric alcohol is advantageous for more stable bubble formation on a thin film resistor in a discharge port of the ink jet head, for providing the biologically active substance.

Also a liquid 12 of the invention containing at least the biologically active substance may contain at least a hydrophilic resin. The hydrophilic resin can be, for example, a natural polymer such as a ligninsulfonic acid salt and shellac, a styrene-acrylic acid-acrylate alkyl ester copolymer salt such as a polyacrylic acid salt, a styrene-acrylic acid copolymer salt, or a styrene-acrylic acid-acrylate ester copolymer salt, an anionic polymer such as a styrene-maleic acid copolymer salt, a styrene-maleic acid-acrylate alkyl ester copolymer salt, a styrene-maleic acid half ester copolymer salt, a styrene-methacrylic acid copolymer salt, a vinylnaphthalene-acrylic acid copolymer salt, a vinylnaphthalene-maleic acid copolymer salt, a β-naphthalenesulfonic acid-formaline condensate salt, or polyphosphoric acid, polyvinyl alcohol, methylolated melamine, polyvinylpyrrolidone, or a cellulose derivative such as methyl cellulose, hydroxymethyl cellulose or carboxymethyl cellulose. In the present invention such resins may be employed singly or in a mixture of two or more kinds. Also there are many other examples, for example a natural resin such as albumin, gelatin, casein, starch, cationized starch, gum Arabic, and sodium alginate. Naturally the present invention is not limited to such examples. By suitably selecting the configuration of a holding layer, it is possible to attain a controlled release of the biologically active substance from the holding layer into a culture liquid. Such controlled release may also be achieved by adding a material capable of realizing a controlled release (for example a water-soluble styrene-acrylic resin) to the liquid containing the biologically active substance. An amount of the substance capable of realizing the controlled release to the liquid containing the biologically active substance is 10 mass % or less, preferably 5 mass % or less. The aforementioned hydrophilic resin is added within a range of 10 mass % or less per kind, preferably 5 mass % or less.

Also the liquid 12 of the invention containing at least the biologically active substance may further include, if necessary for obtaining desired physical properties, a surfactant, a anti-foaming agent, an antiseptic, an inorganic salt, an organic salt and the like. As to the surfactant, any surfactant not detrimentally influencing the biologically active substance for example on a storage stability may be employed, for example an anionic surfactant such as a fatty acid salt, a higher alcohol sulfate ester salt, a liquid fatty oil sulfate ester salt, or an alkylallylsulfonic acid salt, or a nonionic surfactant such as an polyoxyethylene alkyl ether, a polyoxyethylene alkyl ester, a polyoxyethyelensorbitan alkyl ester, acetylene alcohol or acetylene glycol, and these may be employed singly or in a mixture of two or more kinds. Simultaneously with or after the providing of the biologically active substance by the minute droplet discharge means on a desired position of the base 11, the biologically active substance is held on the base 11 and/or a wall 14 and/or a stage 15. For holding the biologically active substance on the base 11 and/or a wall 14 and/or a stage 15, a treatment may be applied in advance to the biologically active substance or to the base 11 and/or a wall 14 and/or a stage 15. For example, a holding area can be formed by applying an aqueous solution of a water-soluble polymer such as gum Arabic, agar, gelatin, starch, tragacanth, crystalline cellulose, methyl cellulose, ethyl cellulose, hydroxypropyl cellulose, hydroxypropyl methyl cellulose, hydroxypropyl methyl cellulose phthalate, cellulose acetate phthalate, polyvinylpyrrolidone, macrogol, polyvinyl alcohol or methacrylic acid copolymer, or a dispersion of organic or inorganic particles employing such polymer as a binder. To immobilize a biologically active substance onto the base 11, the active substance may be subjected to a treatment necessary for immobilization in advance or the base may be subjected to a necessary treatment. Treatment of the active substance includes introduction of a functional group required for covalent bonding such as amino, carboxyl, disulfide, epoxy, carbodiimide, and maleimide, or binding of a chargeable compound necessary for binding through electrostatic attraction such as fine particles of a metal or inorganic oxide, cationic or anionic polymers. A substance that allows binding through biological affinity such as avidin and biotin, and antigen and antibody can be also used. Alternatively, the surface of the base may be coated with a polymer or a silane coupling agent to introduce a functional group necessary for covalent bonding such as amino, carboxyl, disulfide, epoxy, carbodiimide, and maleimide. Alternatively, an electroconductive layer or semiconductive layer mage be formed on the substrate in advance to charge the base surface. The layer may be formed with a metal such as gold, silver, platinum and iron, an inorganic oxide such as indium-tin oxide, titanium oxide and zinc oxide, or an electroconductive polymer such as polyacetylene, polypyrrole, polyaniline and polythiophene. Further, the base is provided with a substance having an affinity with the substance introduced to the biologically active substance, such as biotin, avidin, antibody or antigen, protein A that binds to antibodies. Introduction of such a material makes the binding force between the base 11 surface and the biologically active substance strong.

Energy can be supplied from outside by heating or irradiation for accelerating binding between the base 11 and the biologically active substance. The cell culture substrate 1 can be prepared as explained above.

In the following, there will be explained a cell culture method utilizing the cell culture substrate 1. By culturing cells under such conditions that at least part of the holding areas in the culture substrate 1 comes in contact with the culture liquid at a predetermined point of culture, it is possible to control at least one of cell adhesion, proliferation, differentiation, survival, maintenance of an undifferentiated state and death. The cells are not particularly restricted, but are preferably those of which any of the aforementioned functions may be affected by the held substance. Prior to the cell culture, the cell culture substrate 1 may be sterilized according to necessary, for example, by an ultraviolet irradiation. This operation will prevent contamination of the culture with undesired microorganisms. The cell culture may be conducted by immersing the substrate 1 in the culture liquid. It is possible to carry out cell culture with controlling at least one of the cell properties mentioned above as long as at least part of the holding areas comes into contact with the culture liquid at a certain point of cell culture. Also it is possible to replace the culture liquid or irradiate with light or radiation during or after cell culture on the substrate 1. In this manner it is possible to vary the proliferation or differentiation of the cells or to vary an adhesive property to the substrate. The cell culture may also be carried out by contacting the biologically active substance with a flow of a culture liquid, namely under a circulation of the culture liquid. Also the cultured cells may be removed from the substrate during or after the cell culture on the substrate 1. In this manner the substrate after the removal of the cultured cells can be used again, and the removed cultured cells may be utilized as an artificial tissue or a part thereof.

Such re-use of the substrate is one of the advantages obtained by immobilizing the biologically active substance to the substrate, whereby the cells are unable to incorporate such an immobilized substance into the metabolic system. Also by coating the substrate in advance with a temperature-responsive polymer such as poly(N-isopropylacrylamide) and culturing cells thereon, it is possible to remove the cultured cells by reducing the temperature to about 30° C., causing a change in the hydrophilicity of the polymer surface. In this manner the cells can be utilized, for example, in a live tissue.

For a quantitative determination of a substance synthesized in the cells or a substance incorporated therein, there may be employed a method of measuring an amount of a radiation emitted from a radioactive compound, a method of measuring an amount of fluorescence emitted from a substance labeled with a fluorescent substance, a method of measuring an amount of light emitted from a light-emitting substance, or a method of measuring an absorbance of a dye.

In the method of measuring an amount of a radiation emitted from a radioactive compound, a method employing a compound in which an element abundantly present in a live tissue such as hydrogen, carbon, nitrogen, phosphor or sulfur is replaced by a radioactive isotope, and measuring an amount of radiation emitted from such a compound has a very high sensitivity, and also permits observation of phenomena as in a live body, since such compound is same in chemical properties as in an ordinary compound.

Also a method of labeling with a fluorescent substance is relatively simple and gives little influence on the metabolism of the cells by employing a fluorescent substance of a low molecular weight. Also in a quantitative determination of a substance produced by the cells by a determination method utilizing an antigen-antibody reaction, an evaluation by a fluorescent measurement is effective since antibodies labeled with a fluorescent substance are available in various kinds and provide a high measuring sensitivity.

Also the method of measuring an amount of luminescence emitted from a luminescent substance allows to recognize even a small change, since the luminescence can be measured with a high sensitivity. In case a gene is known that is expressed with adhesion, proliferation, differentiation or substance production induced by the screened substance, it is possible to introduce a luciferase gene or the like in the vicinity of such a gene and an amount of luciferase produced by the gene expression is measured from the intensity of luminescence generated on addition of ATP and luciferin. In this manner it is possible to evaluate the influence of the screened substances from the luminescence intensity.

In a method of measuring the absorbance of a dye, it is possible to amplify the absorbance by employing an enzyme reaction etc. in combination, thereby enabling a quantitative determination of a substance of a very small amount.

EXAMPLES

In the following, the present invention will be clarified further by examples thereof. In the following description, "%" is based on mass unless specified otherwise.

Example 1

The entire surface of a cell culture substrate 1 made of polystyrene was coated with a solution of poly-L-lysine and a dextran activated using tresyl chloride, as an immobilizing crosslinking material.

An ink jet cartridge for a thermal ink jet printer, BJF930 (manufactured by Canon Inc.), was sufficiently washed with a 70% aqueous solution of ethanol. IGF-I dissolved in a 10 mM solution of acetic acid was diluted with a 50% aqueous ethanol solution to a concentration of 50 μm/ml. The obtained IGF-I solution was filled in the cartridge of the ink-jet printer, then discharged and provided on a base 11. The discharge pattern was controlled by a personal computer connected to the printer, and each droplet had a size of about 4 picoliters. The IGF-I solution was discharged onto the base 11 coated with the active dextran, and the substrate was left to stand in a humidified incubator for 12 hours at 4° C. In this manner there was prepared an TGF-I-immobilizing area. In a similar manner, bFGF, bFGF and IGF-I were immobilized with various combinations and different concentrations according to the areas on the base 11. After the immobilization of the biologically active substances, the unreacted active dextran was blocked with a 1% gelatin solution.

On the thus prepared substrate, a murine skeletal muscle cell strain C2C12 was cultured. As a culture liquid, DMEM (Delbucco's modified eagle's minimum essential medium) containing FES (fetal bovine serum) by 2% was used. At first the culture was conducted for 72 hours at 37° C., in humidified air (95-100% RH) containing $CO_2$ by 5%, in a state where the level of the culture liquid was lower than the upper surface of the stage 15. Then the cells were treated with 10% formalin for 15 minutes and then with methanol for 15 minutes. Cells were stained with a fluorescent dye TOTO-3 for DNA and with a primary antibody MF20 and a secondary antibody IRDy800 for muscle differentiation, and fluorescent intensities were measured. Fluorescent intensity of TOTO-3 at 700 nm was employed as an index for the cell proliferation on the substrate, and relative fluorescent intensity of IRDy800 at 800 nm as an index for the muscle differentiation.

The cell proliferation was accelerated in the areas containing bFGF only depending on the concentration, while the muscle differentiation was accelerated in the areas containing IGF-I only depending on the concentration. However, the muscle differentiation was suppressed in the areas containing both factors, indicating that the function of IGF-I was suppressed by bFGF. In this manner it was shown that cell differentiation depends on the kinds and combination of the growth factors, even with two growth factors.

Example 2

Figure 2:
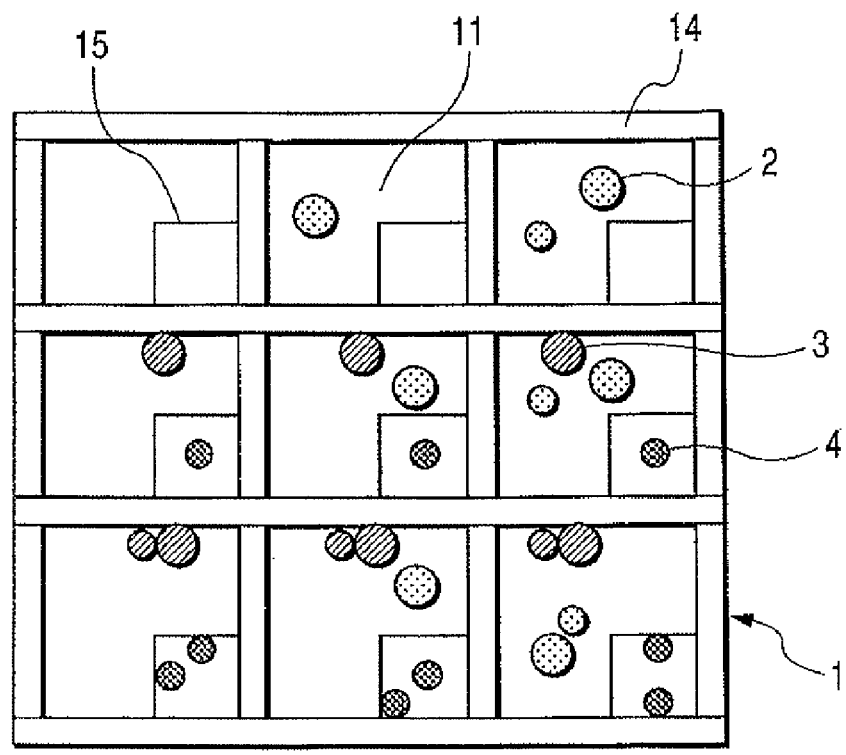
FIG. 2 is a plan view of an example of a cell culture substrate of the present invention.

As shown in FIG. 2, a substrate was prepared employing three growth factors 2, 3, and 4 with different combinations and concentrations on the base 11. bFGF, IGF-I and BMP-2 were immobilized on the base 11 in a similar manner as in Example 1 and held on the stage 15. Then the same culture liquid as in Example 1 was added to immerse the stage 15, thereby re-dissolving all the growth factors on the stage 15.

Then C2C12 cells were cultured on this substrate for 96 hours in the same manner as in Example 1, and relative activity of creatine kinase (CK) as an index for muscle differentiation, and a relative activity of alkali phosphatase (ALP) as an index for bone differentiation were measured.

Results similar to those in Example 1 were obtained in the areas where BMP-2 was not present. With increased concentrations of BMP-2, the relative activity of CK generally decreased and the relative activity of ALP increased. On the other hand, in areas of high BMP-2 concentrations, the relative activity of ALP decreased with bFGF or IGF-I. It was thus clarified that the muscle differentiation was suppressed while the bone differentiation was accelerated by BMP-2, but the function of BMP-2 was suppressed by IGF-I or bFGF.

Next, a culture substrate was prepared holding BMP-2 alone on the stage 15. C2C12 cells were cultured on the substrate in the same manner as above except that BMP-2 on the stage 15 did not come into contact with the culture liquid for the first 24 hours. After 24 hours, fresh culture liquid was so added that the stage 15 was immersed, thereby re-dissolving BMP-2. Thereafter the culture was conducted for further 72 hours, and bone differentiation and muscle differentiation on the substrate were measured.

As a result, the addition of BMP-2 after 24 hours from the start of culture did not accelerate bone differentiation nor suppress the muscle differentiation, indicating that BMP-2 had to be added within 24 hours from the start of the culture, in order to accelerate bone differentiation. In this manner different states of differentiation could be observed by varying the kinds of the growth factors in combination and the acting time thereof.

Example 3

The following process was employed for investigating influence of timing and concentration of a biologically active substance on cells.

IGF-I was employed as the biologically active substance. A solution containing glycerin by 5% and IGF-I at 20 μg/ml was prepared. An ink cartridge was washed with 70% ethanol, and filled with the solution containing the biologically active substance. As in Example 1, the base 11 of a 24 well transparent plastic microplate was subjected to a treatment with active dextran.

Figure 3:
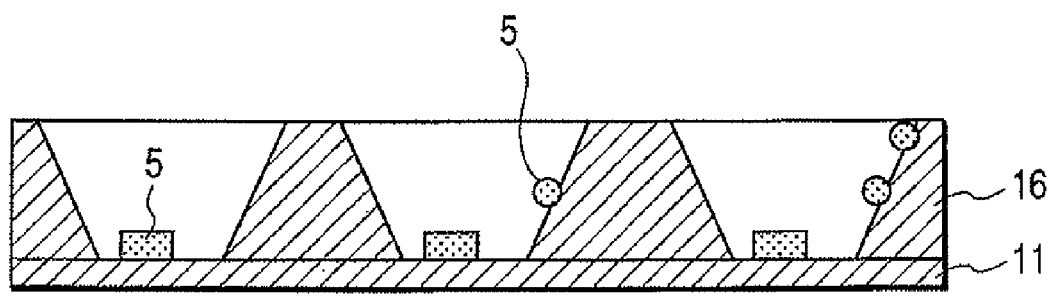
FIG. 3 is a cross-sectional view of an example of a cell culture substrate of the present invention.

As shown in FIG. 3, IGF-I was discharged by an ink jet printer on the base 11 and an inclined wall surface 16. Reference numeral 5 denotes IGF-I. IGF-I was immobilized on the base 11 and held on the wall. After the fixation of IGF-I, the unreacted active dextran was blocked with a gelatin solution. Murine skeletal muscle cell strain C2C12 suspended in DMEM containing 2% FBS was added to the wells of the substrate, thereby allowing action of IGF-I on the base 11 to the cells, and cultured for 96 hours in total at 37° C. and in wet air containing CO2 by 5% with addition of the culture liquid at predetermined times after the start of the culture to dissolve IGF-I on the wall 14.

The culture liquid was added as follows to dissolve IGF-I:
(1) no addition;
(2) addition after 36 hours; or
(3) additions after 36 hours and 72 hours.

The cells after the culture were treated for 10 minutes with 10% formalin, and stained for the enzyme activity of creatine kinase (CK) as an index of muscle differentiation by IGF-I.

As a result, the degree of muscle differentiation varied by the total amount of IGF-I. In the above-mentioned conditions, the stained portion by CK increased in the order of (1)<(2)<(3). This fact indicates that the level of acceleration of muscle differentiation depends on the amount of IGF-I present in the culture liquid. throughout the culture period. Thus influence of the action period of a biologically active substance can be studied using a microsubstrate of the present invention that allows addition of the biologically active substance in a stepwise manner.

Example 4

The following process was employed for investigating influence of the timing of addition and concentrations of the biologically active substance on cells.

IGF-I and bFGF were employed as the biologically active substances. Solutions were prepared to contain 5% glycerin and 20 μg/ml of IGF-I or bFGF. Ink cartridges were washed with 70% ethanol, and filled with the solutions respectively. As in Example 1, the base 11 was subjected to a treatment with active dextran.

Figure 4:
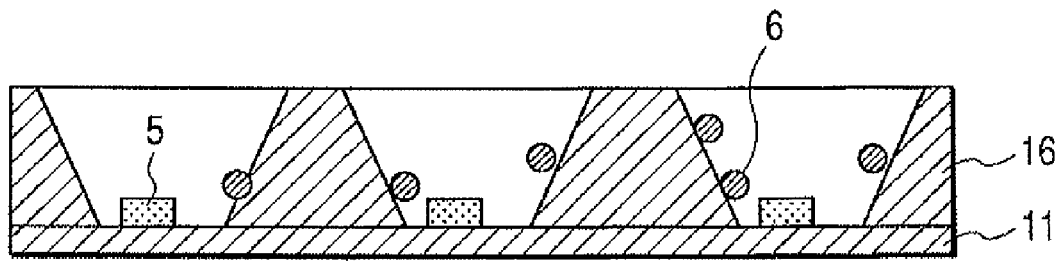
FIG. 4 is a cross-sectional view of an example of a cell culture substrate of the present invention.

As shown in FIG. 4, IGF-I was immobilized on the base 11, and bFGF was held on the inclined wall surface 16 by using an ink jet printer to form 16 combinations of concentrations of IGF-I and bFGF in 80 wells (four concentrations for each growth factor, and five wells for each combination). Reference numerals 5 and 6 denote IGF-I and bFGF, respectively. The murine skeletal muscle cell strain C2C12 suspended in DMEM containing FBS by 2% was added to the base 11. Fresh culture liquid was added at predetermined time lapses from the start of the culture to dissolve bFGF on the wall 14. Cells were cultured for 96 hours at 37° C. and in humidified air containing $CO_2$ by 5%. Addition of fresh culture liquid was conducted as follows:
(1) Immediately after the start of culture;
(2) After 12 hours from the start of culture;
(3) After 24 hours from the start of culture;
(4) After 48 hours from the start of culture;
(5) After 72 hours from the start of culture.

The cells after the culture were treated for 10 minutes with 10% formalin, and subjected to enzyme activity staining for creatine kinase (CK) as an index for muscle differentiation with IGF-I.

As a result, the muscle differentiation was affected by the timing of action of bFGF. Many stained cells were observed where bFGF was not disposed on the wall 14 and where IGF-I was added 48 hours or 72 hours (conditions (4) and (5)), but cells were scarcely stained where IGF-I was added under conditions (1), (2) or (3). Also the number of stained cells decreased as the bFGF concentration increased. This fact indicates that, the muscle cell differentiation is significantly suppressed when bFGF is added within 24 hours from the start of the culture. Thus influence of the action period of a biologically active substance can be studied using a microsubstrate of the present invention that allows addition of the biologically active substance in a stepwise manner.

Industrial Applicability

As explained in the foregoing, the present invention enables to analyze growth factors in a complex multiple system simply and within a short time, and therefore has a wide application in the fields of bioscience, biochemical science and regeneration therapy.

The present invention is not limited to the above embodiments and various changes and modifications can be made within the spirit and scope of the present invention. Therefore, to appraise the scope of the present invention, the following claims are made.

This application claims priority from Japanese Patent Application No. 2003-418560 filed Dec. 16, 2003, which is hereby incorporated by reference herein.

The invention claimed is:

1. A method for screening a cell culture condition utilizing a cell culture substrate having at least one area for culturing a cell on a substrate, the culturing area comprising an area for holding a biologically active substance having a biological activity to the cell and an area for immobilizing a biologically active substance having a biological activity to the cell, the method comprising the steps of:

filling the culturing area with a culture liquid and culturing the cell in a state where the biologically active substance immobilized in the immobilizing area is in contact with the culture liquid;

contacting the culture liquid with the holding area thereby liberating the biologically active substance present in the holding area into the culture liquid, wherein the culturing area is arranged at an open recess of the substrate.

2. The method according to claim 1, further comprising the step of replenishing the culture liquid with a substance necessary for screening the cell culture condition.

3. The method according to claim 1, further comprising the step of observing a shape change of the cell.

4. The method according to claim 3, wherein the cell is stained for evaluation.

5. The method according to claim 1, further comprising the step of carrying out a quantitative determination of a substance synthesized in the cell.

6. The method according to claim 1, further comprising the step of carrying out a quantitative determination of a substance incorporated in the cell.

7. The method according to claim 5, further comprising a step of carrying out a quantitative determination of the substance by at least one of a radiation dose measurement, a fluorescence amount measurement, a light emission amount measurement and an optical absorbance measurement.

8. The method according to claim 6, further comprising a step of carrying out a quantitative determination of the substance by at least one of a radiation dose measurement, a fluorescence amount measurement, a light emission amount measurement and an optical absorbance measurement.

* * * * *